United States Patent [19]

Litt

[11] 4,092,408

[45] May 30, 1978

[54] METHOD FOR SOLID PHASE IMMUNOLOGICAL ASSAY OF ANTIGEN

[75] Inventor: Gerald J. Litt, Wellesley, Mass.

[73] Assignee: New England Nuclear Corporation, Boston, Mass.

[21] Appl. No.: 608,621

[22] Filed: Aug. 28, 1975

[51] Int. Cl.$^2$ .......................... G01N 33/00; B01J 1/22; A61K 43/00
[52] U.S. Cl. ..................................... 424/1; 23/230 B; 23/259; 424/12
[58] Field of Search .................. 23/230 B, 259; 424/1, 424/12

[56] References Cited

U.S. PATENT DOCUMENTS

| 3,876,504 | 4/1975 | Koffler | 23/230 B X |
| 3,896,217 | 7/1975 | Johnson | 424/1 |
| 3,904,367 | 9/1975 | Goubersuch | 23/230 B |
| 3,979,509 | 9/1976 | Giaever | 23/230 B X |

Primary Examiner—Benjamin R. Padgett
Assistant Examiner—Christine M. Nucker
Attorney, Agent, or Firm—Sewall P. Bronstein

[57] ABSTRACT

An improved solid-phase radioimmunological assay method for assay of an antigen in a biological fluid, e.g., blood plasma, by use of a solid phase polymeric substrate on which is adsorbed in solid phase an antibody composite layer, comprising a solid phase precoat of an anti-antibody (Ab$^2$) (i.e., an antibody to an animal blood serum and sometimes referred to as a second antibody) bound to said substrate and a solid phase antibody Ab specific to said antigen (sometimes referred to as a primary antibody) immunologically bound to said antiantibody precoat. The biological fluid to be tested, containing the antigen and radioactive labelled antigen, is contacted with the antibody surface of the composite layer to immunologically bind antigen and radioactive labelled antigen to the solid phase Ab surface, whereupon the quantity of antigen in the biological fluid is determined by measuring the radioactivity of the composite layer and substrate or of the remaining biological fluid containing unbound antigen and unbound radioactive labelled antigen.

An improved method for making as an article of manufacture solid phase antibody (Ab) for radioimmunological assay of antigen by first adsorbing Ab$^2$ from its serum on a solid substrate to produce a solid Ab$^2$ precoat and then reacting the Ab$^2$ precoat with Ab in its antiserum to form a solid phase Ab coating on the Ab$^2$ precoat whereby an effective, efficient, reproduceable and stable solid phase antibody Ab for assay of antigen is obtained with a substantial decrease in the amount of Ab required.

The terms coating, precoating, coat and coating do not necessarily mean continuous or complete coat or coating of the underlying surface but, instead, include continuous and non-continuous coatings.

10 Claims, 1 Drawing Figure

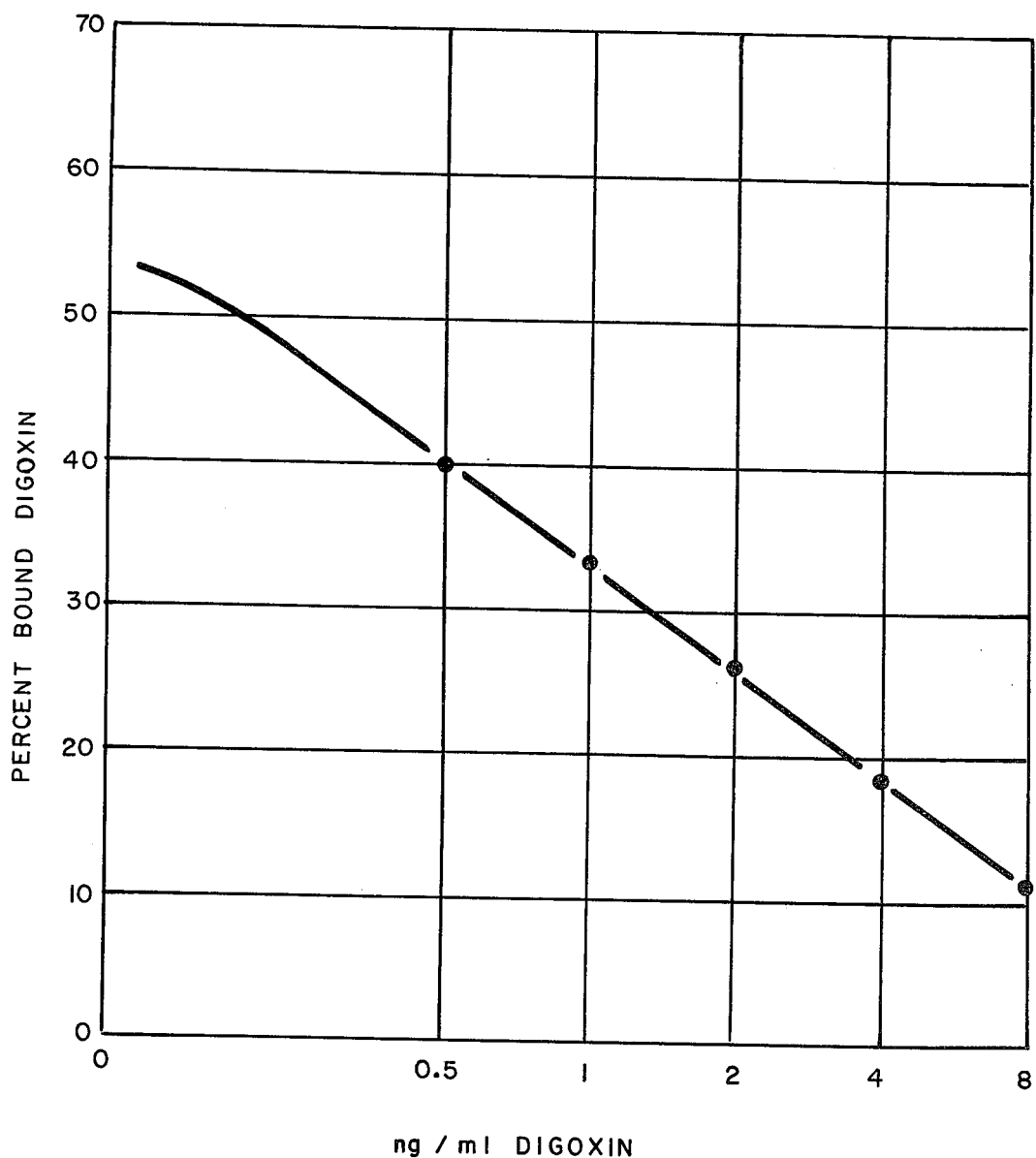

METHOD FOR SOLID PHASE IMMUNOLOGICAL ASSAY OF ANTIGEN

BACKGROUND OF THE INVENTION

The invention relates to an improved solid phase immunological (preferably radioimmunological) assay method for the quantitative determination of antigens (Ag), e.g., hormones such as insulin, drugs such as digoxin, steroids such as the estrogens, etc. in a biological fluid, e.g., biological fluids from the body of an animal, such as blood serum, plasma, urine, gland extracts or gastric juices.

It also relates to an improved method for making as an article of manufacture an improved solid phase antibody (Ab) for use as such in carrying out said immunological assay method.

It also relates to a kit which includes tubes containing the improved solid phase antibody, a vial containing radioactive labelled antigen specific to the antibody, a vial containing buffer solutions to use clinically for assay of antigen and vials containing standard antigen amounts for preparation of a standard calibration curve, all packaged in a compact container.

Antigens (Ag) are substances which are capable by themselves or in combination with other substances of inducing the formation of specific antibodies (Ab) against themselves in an organism, e.g., in the body of an animal, into which they are introduced or in which they are formed to thereby neutralize the effect of the antigens.

Antibodies (Ab) are usually blood serum proteins of the globulin fraction, specific ones of which are formed in response to the introduction into the organism of specific antigens and which usually have substantially greater molecular weights than their antigens. The antibody neutralizes the effect of its antigen by binding the antigen to itself. The antibody (Ab) for a specific antigen (Ag) may be prepared by injecting the Ag into a rabbit or other animal. The animal produces the antibody to the antigen and the animal's blood can be processed (basically removal of red blood cells) to produce the antiserum containing the antibody.

In radioimmunological assay methods, which do not employ solid phase antibody, reaction (incubation) of solutions of non-labelled and labelled antigen Ag with solutions of antibody Ab forms a soluble Ab-Ag complex (the antigen becomes bound to the antibody) of relatively large molecular weight and size. Typically, porous solid materials such as charcoal are used onto which is adsorbed the labelled and non-labelled antigen of relatively small molecular weight and size, but not the Ab-Ag complex of larger molecular weight and size. By removing the supernatant from the charcoal and measuring the radioactivity of the charcoal containing unbound labelled and unlabelled antigen, or the supernatant containing bound unlabelled antigen and labelled antigen, quantitative measurement of the antigen in the biological fluid being tested can be achieved.

The use of solid phase antibody, e.g., as a solid layer, to react with the antigens has certain obvious advantages over the aforesaid non-solid phase techniques.

Since the present invention is directed to radioimmulological assay techniques employing solid phase antibodies, the discussion will be directed principally to these techniques.

Such techniques may be categorized into two classes: one is called IRMA, in particular, 2-site IRMA, and the other RIA.

Both solid phase antibody techniques are characterized by the pretreatment of a solid phase substrate surface, usually a polymeric tube or disc capable of adsorbing antibodies, with a solution of a specific antibody (Ab) for the antigen (Ag) to be assayed to effect adsorption or binding of the antibody as a solid phase layer to the substrate surface, to thereby achieve a solid phase antibody (Ab) surface. In effect, the Ab is precipitated out of solution onto the substrate as a solid phase Ab layer. The resulting solid phase antibody (Ab) is utilized in the quantitative determination of its antigen.

The IRMA technique utilizes radioactively labelled antibody whereas the RIA technique utilizes radioactively labelled antigen.

In the 2-site IRMA technique non-labelled antigen (Ag), in solution in the biological fluid being assayed, is reacted (incubated) with the solid phase antibody (Ab) to bind the Ag as a solid phase to the solid phase Ab followed by reaction (incubation) of the resulting solid phase antigen with radioactively labelled antibody (Ab*) whereby the Ab* becomes bound in solid phase to the solid phase antigen.

In the RIA technique, the radioactively labelled antigen (Ag*) and unlabelled antigen Ag are reacted or incubated with the solid phase Ab to form solid phase labelled and unlabelled antigen bound to the solid phase Ab.

These IRMA systems are discussed in Miles et al, "Properties of Two-Site Immunoradiometric (Labelled Antibody) Assay Systems", IAEA, 149, (1974), incorporated herein by reference.

Solid phase RIA systems are disclosed in U.S. Pat. Nos. 3,790,663, 3,646,346 and 3,826,619 as well as Catt et al, Science 158, 1570 (1967), all incorporated herein by reference.

All of the aforesaid solid phase radioimmunological techniques have disadvantages both in manufacture of the solid phase antibody and in clinical assay.

A common disadvantage is that relatively large concentrations and amounts of Ab are required to form the solid phase Ab. Specific antibodies Ab for specific antigens are often difficult to obtain continuously and consistently, particularly in the case of those antigens which are poor immunogens. For example, out of 100 rabbits injected with a specific antigen, a large number may not build up any specific Ab for that antigen at all and others may build up only a small amount. Accordingly, the supply of specific antibody is erratic, relatively expensive and sometimes tight. Therefore, there has been a long felt need for a method of making solid phase Ab utilizing substantially smaller concentrations and amounts of Ab.

The IRMA techniques require even more Ab than the RIA techniques because they employ radioactively labelled antibody Ab*. The IRMA procedure is also sensitive to serum effects during assay and is beset by the potential of antigen exchange via dissociation from the solid phase, i.e., during the reaction of the Ab* solution with the solid phase Ab-Ag, the previously deposited solid state Ag may dissociate from the solid phase. Such exchange would limit assay dose-response, particularly at high antigen concentrations.

Relatively large concentrations and amounts of Ab are required to form the solid phase Ab layer in present solid phase procedures in order to insure consistently adequate uniform and reproducible adsorption or deposit of Ab on the substrate to adequately and uniformly and consistently sensitize the solid phase substrate for uniform consistent and reproducible assay results. Different surface effects of the substrate tend to cause non-reproducible and non-uniform binding patterns and quantities (of the antibody to the substrate and hence of the antigen to the antibody) which effects the reproducability of assay results. More specifically, a relatively uniform and adequate amount of Ab must be consistently adsorbed on the substrate in order to achieve consistently adequate uniform and reproducible results and such uniformity is difficult to consistently achieve because of the different surface effects of the substrate.

Cocola et al in "New Radioimmunoassay Technique Using Second Antibody to Solid Phase Applied to Assays of Human Chorionic Somatomammotropin" Jour. Nucl. Biol. Med. 17, 174 (1973) discloses a procedure wherein solid phase anti-antibody $Ab^2$, i.e., an anti-body built up in an animal against the serum of another animal, is adsorbed from solution as a solid phase on the substrate followed by contact of the resulting solid phase $Ab^2$ with a solution of Ab and Ag to which a radioactive labelled antigen (Ag*) is subsequently added while still in contact with the solid phase $Ab^2$. According to Cocola, the Ab, Ag and Ag* form soluble complexes Ab-Ag-Ag* which become bound as a solid phase to the solid phase $Ab^2$.

The anti-antibody $Ab^2$ is usually obtained immunologically by injecting the blood plasma or serum of one animal (e.g. a rabbit) into another animal, e.g., a sheep or goat, which builds up antibodies $Ab^2$ against the serum of the rabbit. These anti-antibodies may be recovered from the sheep's blood as anti-antiserum containing the $Ab^2$.

The term titre in the art means that amount of Ab which will result in about 50% binding of labelled antigen to Ab.

As aforesaid, antiserum containing Ab is obtained from the blood by separating out the red blood cells usually by centrifugation leaving the serum containing the antibody. This antiserum which may be further fractioned, is diluted with aqueous diluent (usually saline or buffer solutions) to various dilutions. A dilution of 1:50000 for example, means that the antiserum has been diluted to a ratio of 1 ml antiserum to 49,999 ml of diluent. A titre of 1:50000 means that dilution of antiserum is required to achieve about 50% binding of labelled antigen to Ab.

Cocola used an $Ab^2$ titre or 1:10 to 1:50 and an Ab titre of 1:64000. Due to the comparative slowness of the immunogenic reaction (incubation) between the solid phase second antibody $Ab^2$ and the mixture in solution of Ab, Ag and Ag*, Cocola's method requires an 18–24 hour clinical incubation period. This lengthy clinical incubation substantially limits the use of such technique in clinical applications.

The aforesaid Miles publication discloses in the IRMA technique, using radioactive labelled antibody Ab*, that the Ab, before reacting with Ag followed by reaction with Ab*, may be bound to the substrate surface by intermediate immunoglobulin arms either in the form of non-immune guinea-pig immunoglobulin (GP, IgG), as such, or as a rabbit-anti (GP IgG) in order to minimize serum effects during assay and improve dose response, his conclusion being that at least two arms are required to achieve this. This technique undesirably requires two clinical incubations (Ab-Ag and Ag-Ab*) and also a relatively large amount of Ab since it requires labelled Ab during assay in addition to the previously produced Ab.

STATEMENT OF THE INVENTION

The present invention is predicated upon the discovery that by adsorbing $Ab^2$ from solution in its anti-antiserum and as a solid phase precoating on the substrate followed by adsorbing Ab from its antiserum and as a solid phase coating on the $Ab^2$ coating, followed by carrying out the radioimmunological assay of antigen by contacting the resulting solid phase Ab surface of the double coated substrate with the biological fluid, containing antigen to be assayed and radioactive or fluorescent or enzyme labelled antigen, to cause antigen and labelled antigen to become bound in solid phase to the solid phase Ab surface and followed by measuring radioactivity or fluorescense or enzyme activity of the solid phase bound antigen or of the unbound antigen remaining in solution, important advantages are achieved over known RIA and IRMA solid phase techniques.

One of the most important advantages is that the dilution and amount of primary antibody (Ab) titre can be sharply reduced, in some cases by more than 10 times to dilutions as low as about 1:1,500,000. This is an important manufacturing (manufacture of solid phase Ab) advantage in view of the high cost of, and supply difficulties with, primary antibodies, particularly in the case of antibodies for antigens which are poor immunogens.

Secondly, only very dilute solutions, and hence small amounts of anti-antibody $Ab^2$ are required as low as 1:10000. This is not as important as the reduction in antibody Ab dilution since anti-antibodies are much more easily obtained in adequate supply and it is not necessary to have a specific anti-antibody for any specific antigen or for any particular antiserum.

Thirdly, clinical assay time is reduced as compared with Cocola's RIA technique and Miles IRMA technique. This is an important clinical advantage.

Fourthly, only one clinical incubation is required as compared to IRMA techniques. This is an important clinical advantage.

Fifthly, the solid phase Ab and $Ab^2$ of the composite $Ab^2$-Ab layer on the substrate (the substrate with the solid phase $Ab^2$-Ab composite layer is an article of manufacture manufactured at the manufacturing site and shipped, as such, or as part of a kit for clinical assay) is highly stable and can be stored for long periods of time and shipped long distances without harmful effect. This is an important manufacturing advantage.

Sixthly, clinical assay procedure has the simplicity of the Catt technique (adsorption of Ab in solid phase and from solution on the substrate surface followed by contact of the resulting solid phase Ab with Ag and Ag* in solution to form solid phase Ag and Ag* bound to the solid phase Ab followed by radioactive measurement of bound Ag* or unbound Ag*), as compared with the Cocola and IRMA techniques, without many of the disadvantages of the Catt technique, namely (1) the manufacturing and economic difficulties resulting from the necessity of larger concentrations of primary antibody (Ab), (2) the difficulty of consistently achieving uniform and adequate Ab coatings which will consistently, reproducibly and adequately sensitize the substrate to consistently achieve uniform and reproducible assay results over a wide range of antigen concentrations for a number of different antigens and (3) sensitivity to the presence of proteins other than the Ab in the antiserum. These protein impurities tend to take up substrate binding sites to thereby remove them as binding sites for the Ab.

Seventh, the antibody Ab need not be purified before incubation with the solid phase $Ab^2$.

The dual coated substrate is preferably sold as part of a kit, which also includes sealed vials of buffer solution and of tracer labelled antigen and of antigen standards for use in clinical assay.

DESCRIPTION OF THE DRAWINGS

FIG. 1 shows a standard curve obtained by measuring the percent of bound antigen (bound to solid phase Ab) with a plurality of solutions containing known but different amounts of antigen (digoxin) and the same amount of labelled antigen ($^{125}I$- digoxin) and otherwise being the same in composition, and plotting these percentages along the ordinate against the log of the antigen concentrations in ng/ml of the solutions along the abscissa, using a dual coated ($Ab^2$-Ab) substrate according to the invention (see Section D of the Example).

DESCRIPTION OF THE MATERIALS AND PARAMETERS

The present invention can be advantageously used for quantitative assay of any antigen. Examples of antigens include, but are not limited to, drugs such as digoxin, cortisone, etc., toxins such as tetanus toxin, steroid hormones, such as estrogens and testosterone, polypeptide protein hormones such as insulin, human growth hormone (HGH), thyroid stimulating hormone (TSH), human chorionic gonadotropin (HCG), luteinizing hormone, follicle stimulating hormone (FSH), human placental lactogen (HCS) and the angiotensins and other hormones.

The solid substrate useful in the invention can be any of those known in the solid phase RIA and IRMA arts for adsorbing antibodies. It can have any physical shape but it is usually in the form of a tube or vial, disc or stick. It can be of any material capable of adsorbing antibodies but is usually a polymeric material, including, but not limited to, polymers of styrene, such as polystyrene and styrene acrylonitrile copolymer, ethylene, propylene, and other alkenes and acrylates and cellulosic polymer such as nitrocellulose and other polymers disclosed in U.S. Pat. No. 3,790,663 incorporated herein by reference.

A preferred form of substrate is a polymeric tube to which the $Ab^2$ anti-antiserum can be initially added to form the $Ab^2$ precoat on the inner surface of the tube followed by adding the Ab antiserum to form the solid phase Ab coat on the solid phase $Ab^2$ precoat followed by sealing and storage and shipping and then by adding the biological fluid containing the unlabelled antigen to be assayed, and the labelled antigen to bind the antigens to the solid phase Ab coat. However, a dipstick which is immersed in the various solutions during coating and assay, is also preferred.

The substrate may be of any material lined with an Ab-binding polymer.

The anti-antibody ($Ab^2$) employed in accordance with this invention can be any of those known in the art and can be prepared by any immunological method known in the art. For example, as aforesaid, such preparation may be effected by injections of small amounts of any blood serum from any animal, usually in combination with adjuvants such as Freund's mineral oil emulsion, into another animal. The anti-antiserum containing $Ab^2$ produced by the other animal against the injected serum can be recovered from the blood of such animal by conventional means and purified by conventional methods. The serum of the first animal need not contain an antibody specific to the antigen being assayed. In fact, it need not contain any specific antibody at all.

The primary antibody of antiserum (Ab) can be any known antibody specific to the antigen to be assayed and can be prepared by immunization of animals with small quantities of the antigen to be assayed in a conventional manner. Preferably, such primary antiserum is not purified when used in accordance with this invention, but it can be.

The solid phase anti-antibody ($Ab^2$) precoat is prepared by contacting the substrate (preferably the inside surface of the tube or vial) with a highly diluted, and preferably purified and buffered, anti-antiserum during an incubation period (usually 18 hours or overnight) at room temperature whereby the $Ab^2$ in the anti-antiserum is adsorbed on and becomes bound to the substrate surface as a solid phase $Ab^2$ precoat or layer.

Preferred $Ab^2$ anti-antiserum dilutions are between 1:1000 to 1:10000 for certain antigens, such as digoxin and estriol, but go as low as 1:100 for other antigens, such as angiotension I. Although the concentration of the diluted anti-antiserum can be greater (dilutions of 1:20 have been used successfully) this minimizes an advantage of the process since the results achieved are not improved and the cost is increased. Broadly speaking, the dilution should preferably not be decreased below that (the titre) at which about 50% binding of the antigen to the subsequent solid phase Ab coat is achieved at equilibrium. This can be easily and routinely determined by varying the concentration of the anti-antiserum to determine that concentration at which about 50% binding of antigen to the subsequent solid phase Ab coat occurs.

Any known diluents for diluting antiserum (usually saline or buffer solutions) can be used for diluting the anti-antiserum and any known buffers for buffering antiserum can be used to buffer the anti-antiserum.

After the adsorbed solid phase $Ab^2$ precoat has been formed on the substrate, it is thoroughly rinsed, e.g., with saline or buffer solution or any other known rinse (usually they contain saline or buffer, a protein and an antibacterial agent) for rinsing solid phase antibody Ab, to remove non-adsorbed $Ab^2$.

The solid phase antibody Ab coating on the solid phase $Ab^2$ precoat is effected by contacting the solid phase $Ab^2$ while bound to the substrate with an unpurified highly diluted antiserum, containing primary antibody Ab, during an incubation period (usually 18 hours or overnight) at room temperature whereby the Ab reacts with and becomes bound to the solid phase $Ab^2$ surface as a solid phase Ab coat or layer. The dilution of the primary antibody antiserum depends upon the particular antigen system, but for the antigen systems which have been evaluated, it has been found that a substantially reduced concentration (titre) is required as compared to the Catt system. For digoxin antigen, preferred Ab antiserum dilutions are about 1:100,000 to 1:1,000,000 and more preferably about 1:500,000 to 1:900,00 whereas with the Catt system, the titre is about 1:80,000 with the same antigen and antibody. For angiotension I preferred Ab antiserum dilutions are about 1:10000 to 1:100,000 whereas with the Catt system substantially higher Ab concentrations are required to achieve the same % binding of antigen.

Any conventional diluent for diluting antiserum can be used.

The solid phase Ab layer is then rinsed one or more times with a conventional rinse for solid phase antibody.

Other incubation temperatures (4° C to 45° C have been used) and incubation times (one hour to 48 hours have been used) can be employed, the incubation time in each case being greater for lower temperatures. The incubation temperatures and times should not be so great as to harm the anti-antibody or antibodies being incubated but should be great enough to achieve substantial equilibrium in each case. Ordinarily, it is desirable to use the shortest incubation time possible at room temperature.

To effect antigen assay employing the improved solid phase composite $Ab^2$-Ab layer of this invention, a mixture comprising a diluted aliquot of animal serum containing dissolved antigen to be assayed and a known aliquot of the same antigen, conventionally labelled with a suitable isotope or fluorescent or enzyme, is contacted at optimum temperature conditions for the particular antigen system with the solid phase Ab surface for an appropriate period of time, e.g., for digoxin about 1 hour at 37° C, and for estriol, 2 hours at 4° C, to effect antigen insolubilization by binding of the tracer labelled and unlabelled antigen to the solid phase Ab surface. The amount of antigen present in the serum is determined by measurement of the tracer activity of either the solid phase $Ab^2$-Ab coated substrate containing the bound antigen and bound labelled antigen or by measuring the remaining serum-containing liquid containing unbound labelled and unlabelled antigen. Such measurement is achieved by conventional measuring devices such as crystal scintillation counters (in the case of radioactive label). The measurements are compared with a standard plot to determine the amount of antigen in the serum as described more fully below.

The tracer label may be a radioactive isotope, such as $^{125}I$, $^{131}I$, $^{14}C$, $^{3}H$ $^{57}Co$ $^{75}Se$, etc., or a fluorescent particle, such as a fluorescent stilbene or quinine, or an enzyme, such as B- galactosidase, molecularly bound to the antigen.

With a fluorescent label, measurement of bound or unbound labelled antigen is achieved by any convention fluorescent spectrometer. With an enzyme label, measurement of labelled antigen is achieved by measuring enzyme activity. This is conventionally done colormetrically by contact with a colorless o-nitrophenol dyed sugar and measuring the change in color intensity caused by cleavage of the sugar from the dye by reaction of the sugar with the enzyme label to thereby release the dye.

Each time an assay is to be clinically made for any particular antigen, the aforesaid standard plot is clinically prepared for that antigen.

In a preferred embodiment, the solid phase $Ab^2$ and Ab layers are applied to the inner surfaces of a plurality of polymeric tubes. They are shipped in the form of a kit together with sealed vials of buffer solution and of labelled antigen solution and with vials of standard antigen solutions. A sufficient number of tubes of the solid phase $Ab^2$-Ab composite layer and of labelled antigen and buffer and standards are included for the standard plots or graphs to be prepared at the clinic site, as well as a number for clinical assays.

EXAMPLES

PART A — PURIFICATION OF ANTI-ANTIBODY ($Ab^2$)

25 ml of standard sheep-anti rabbit antiserum (obtained in a conventional manner by injecting a sheep with blood serum of a rabbit to build up in the sheep a sheep-anti rabbit anti-antibody $Ab^2$ followed by recovery from the sheep of the anti-antiserum containing the anti-antibody $Ab^2$) was combined with 25 ml of 2% Rivanol (this is a lactate which combines with albumin in the anti-antiserum to precipitate it out). The combination was adjusted to pH 7.4 by the addition of 25 ml of a 0.1 M aqueous solution of sodium phosphate buffer, and allowed to come to equilibrium at ambient temperature for 30 minutes. The resultant precipitate (Rivanol - albumin complex) was separated and discarded. The supernatent was combined with sodium chloride to effect a 5% aqueous solution of sodium chloride and the resultant precipitate (Rivanol) discarded. An equal volume of saturated ammonium sulfate aqueous solution was added to the supernatent and the resulting precipitate containing the $Ab^2$ isolated (the supernatant contains Rivanol). The precipitate containing the $Ab^2$ was redissolved in the minimum amount of 0.9% sodium chloride aqueous solution to effect dissolution. Precipitation is again effected with an equal volume of saturated ammonium sulfate aqueous solution. The precipitate (containing the $Ab^2$) was again redissolved in the minimum amount of 0.9% sodium chloride aqueous solution to effect dissolution and the resulting solution was placed in a dialysis bag and dialyzed against 13 liters of 0.9% sodium chloride solution on the opposite side of the dialysis bag under refrigeration. The last mentioned sodium chloride solution was replaced 2-3 times over the 48 hour dialysis period. This removed soluble impurities, such as salts, which pass through the dialysis bag. The resultant solution in the dialysis bag containing the $Ab^2$, was reconcentrated to its initial 25 ml volume via ultra-filtration and sterily filtered into sterile glass vials. Such vials are stored at 4° C.

PART B — PREPARATION OF PRIMARY ANTIBODY (Ab)

Standard unpurified rabbit-anti digoxin antiserum (obtained by injecting a rabbit with a digoxin-human serum-albumin conjugate and recovering the antiserum) was diluted 1:1000 in 0.9% sodium chloride and 0.05% gelatin aqueous solution in a sterile glass vial. The gelatin prevents adsorption of the antibody to the glass walls.

The Ab may be purified as in Part A but it is not necessary and indeed there is an advantage in not purifying in that the albumin impurity binds with exposed binding sites on the substrate which have not become bound with $Ab^2$, thereby tending to reduce the Ab which might otherwise bind to such exposed sites.

PART C — PREPARING SOLID PHASE $Ab^2$

The purified and sterile sheep-anti rabbit anti-antiserum of Part A was diluted to 1:1000 with a 0.9% aqueous solution of sodium chloride of pH between 7.0 to 7.5. This stock solution was further diluted to 1:7000 with a 0.9% sodium chloride and 0.1% sodium azide aqueous solution. 0.7 mls of the resultant 1:7000 dilution of the purified $Ab^2$ anti-antiserum was added to untreated 12 X 75 mm polypropylene tubes (Sarstedt Corp) and allowed to stand overnight (incubate) at room temperature whereby the $Ab^2$ was adsorbed as a solid phase precoat on, and became bound to, the inside surface of the polypropylene tubes. After such incubation, the precoat solution was aspirated out of the tubes and the tubes were then rinsed and aspirated twice with 0.8 ml of an 0.9% sodium chloride, 0.05% gelatin and 0.1% sodium azide aqueous solution to remove unbound anti-antiserum ($Ab^2$). The gelatin binds to exposed binding sites on the substrate not occupied by $Ab^2$ to thereby minimize the chance of the subsequent Ab binding to such sites.

PART D — PREPARATION OF PRIMARY SOLID PHASE Ab COAT ON $Ab^2$ PRECOAT

The anti-serum containing the primary antibody Ab (rabbit anti-digoxin serum) of Part B was further diluted to a 1:800,000 dilution with a 0.9% sodium chloride, 0.05% gelatin and 0.1% sodium azide aqueous solution. 0.5 mls of the 1:800,000 diluted antiserum was pipetted into the $Ab^2$ precoated tubes prepared in accordance with Part C and allowed to stand (incubate) at ambient temperature overnight (about 18 hours) whereby the Ab was reacted as a solid phase coat with, and became bound to, the $Ab^2$ precoat surface. The remaining dilute antiserum was aspirated out of the tubes and the tubes were rinsed twice, aspiration of the rinse out of the tubes following each rinse, with 0.8 ml of an 0.9% sodium chloride, 0.05% gelatin and 0.1% sodium azide aqueous solution. The dually coated tubes were then air dried and were ready for shipment for clinical assay. The resulting tubes could be stored at room temperature for extended periods of time without deterioration of the solid phase antibodies.

PART E — PREPARATION OF STANDARD CURVE

Sixteen tubes prepared as above were numbered 1 - 16 and the following added:

| Tube # | Human Blood Serum | Patient Serum | Standards in Human Blood Serum | Buffer | Tracer |
|---|---|---|---|---|---|
| 1,2 | — | — | — | — | 0.1 ml |
| 3,4 | 0.05 ml | — | — | 0.4 ml | 0.1 ml |
| 5,6 | — | — | 0.05 ml, 0.5 ng/ml | 0.4 ml | 0.1 ml |
| 7,8 | — | — | 0.05 ml, 1 ng/ml | 0.4 ml | 0.1 ml |
| 9,10 | — | — | 0.05 ml, 2 ng/ml | 0.4 ml | 0.1 ml |
| 11,12 | — | — | 0.05 ml, 4 ng/ml | 0.4 ml | 0.1 ml |
| 13,14 | — | — | 0.05 ml, 8 ng/ml | 0.4 ml | 0.1 ml |
| 15,16 | — | 0.05 ml | — | 0.4 ml | 0.1 ml |

The 0.05 ml human blood serum was free from the antigen to be tested (digoxin).

The standards are increasing known amounts of digoxin in 0.05 mls of the same human blood serum.

The buffer in each case was 0.4 ml of a 0.10 M phosphate and 0.2% BSA (bovine serum albumen) aqueous solution, pH 7.4.

The tracer in each case was 0.1 ml of a buffered aqueous solution of $^{125}$I-digoxin containing 13000 DPM (disintegrations/minute) $^{125}$I-digoxin (approximately 5 pg) and 0.10 M sodium phosphate and 0.2% BSA pH 7.4.

The buffer solution, tracer solution and standards (including the human blood serum) are supplied, with the dually coated $Ab^2$-Ab tubes, in separate vials as part of a kit.

The contents of each of the tubes 1-14 were mixed with a vortex mixer then placed in a water bath at 37° C for 1 hour to achieve Ag-Ab and Ag*-Ab reaction. After removing the incubated tubes from the water bath, they were aspirated to remove the contents and rinsed twice with water. The radioactivity of all the tubes was counted in conventional manner using a well known crystal scintillation counter. The percent of antigen (digoxin) bound to each tube was calculated by comparing the scintillation counts per minute (CPM) for each tube to that of the mean CPM of tubes 1 and 2, i.e.

$$\% \text{ Bound Digoxin} = \frac{\text{CPM}}{\text{Mean CPM of tubes 1 and 2}} \times 100$$

The percent bound digoxin for each duplicate set of tubes was plotted versus the logarithm of the amount of digoxin in the standards in human blood serum to effect the standard curve to be used in completing the assay. Such curve is displayed in FIG. 1.

PART F — ASSAY OF THE Ag IN THE PATIENTS SERUM

To tubes 15 and 16 was added 0.05 ml of the patient's serum, 0.4 ml of the buffer solution and 0.1 ml of the buffered tracer solution. The contents were mixed in the vortex mixer, incubated, aspirated, and rinsed exactly as in Part E and at the same time. The resulting tubes were counted and the average % bound digoxin determined as Part E. The amount of digoxin in ng/ml in the patient's serum was determined by interpolation from the standard curve.

Example I was repeated a number of times. Assay uniformity, reproducability and accuracy were excellent. For comparison, the aforesaid Catt technique (omission of the solid phase $Ab^2$ precoat) was used with the same rabbit-antidigoxin antiserum dilution of 1:800,000. The Ab binding was so poor that satisfactory assay results using the same antigen could not be achieved.

Example I was repeated with excellent results using angiotensin I antigen with an antiserum dilution of 1:60,000 and with an Ab incubation time of 24 hours at room temperature and with different known assay buffers and rinses and diluents and incubation parameters compatible with the angiotensin I being assayed. The anti-antiserum was the same but its concentration was 1:100. When the Catt technique was used with the same dilution of anti-serum the % binding of antigen was about one-half that obtained in accordance with the invention.

The polymer tubes, with the $Ab^2$-$Ab^1$ composite layer bound thereto, may be evacuated and hermetically sealed at the time of manufacture to provide a constant atmosphere in contact with the Ab surface. They may also be sterilized or manufactured sterilely.

The following U.S. Patents not referred to above relate to immunological assay:

| | |
|---|---|
| 3,645,687 | 3,652,761 |
| 3,663,684 | 3,708,572 |
| 3,770,380 | 3,721,528 |
| 3,793,445 | 3,825,410 |
| 3,853,987 | 3,852,415 |
| 3,464,798 | 3,809,782 |

| -continued | |
| --- | --- |
| 3,697,638 | 3,709,868 |

None of them disclose reaction of Ag and Ag* with the solid Ab surface of a solid phase substrate-Ab$^2$-Ab with subsequent measurement of bound solid phase or unbound Ag* to achieve assay.

I claim:

1. An improved method for solid phase immunological assay of an antigen comprising
    (a) contacting anti-antiserum containing anti-antibody with a substrate surface capable of adsorbing said anti-antibody to form solid phase anti-antibody bound to said substrate surface
    (b) incubating said solid phase anti-antibody while bound to said substrate with antiserum containing antibody to form solid phase antibody bound to said solid phase anti-antibody
    (c) incubating said solid phase antibody, while bound to said solid phase anti-antibody and said substrate, with a solution containing antigen specific to said antibody and the same antigen labelled with a tracer, to form solid phase antigen and solid phase tracer-labelled antigen bound to said solid phase antibody and
    (d) measuring the tracer activity either of said solid phase antibody-anti-antibody-substrate or of the remaining solution.

2. The method according to claim 1 wherein said immunological assay is a radioimmunological assay and said tracer is a radioactive substance.

3. The method according to claim 2 wherein said antigen is a digoxin antigen and said antiserum is diluted to between about 1:100,000 and 1:1000000.

4. A method according to claim 2 where said anti-antiserum is diluted to between about 1:100 and 1:10000.

5. A method according to claim 2 wherein the substrate is a polymer.

6. A method according to claim 5 wherein said polymer is selected from the group consisting of a polymer of styrene, a polymer of ethylene, a polymer of propylene and an acrylic polymer and a cellulosic polymer.

7. A method according to claim 6 wherein said substrate is a polypropylene or a polystyrene tube.

8. A method according to claim 2 wherein said antiserum is unpurified.

9. A method according to claim 2 wherein said radioactive substance is $^{125}$I.

10. As an article of manufacture, a solid phase radioimmunological assay kit comprising a plurality of tubes having an internal substrate surface having bound thereto solid phase anti-antibody to which is bound solid phase antibody and a plurality of vials containing radioactive labelled antigen specific to said antibody, antigen standards, and a buffering solution.

* * * * *